(12) United States Patent
Hogg et al.

(10) Patent No.: US 8,361,591 B2
(45) Date of Patent: *Jan. 29, 2013

(54) PACKAGING WITH ACTIVE PROTECTION LAYER

(75) Inventors: Andreas Hogg, Neuchatel (CH); Herbert Keppner, Colombier NE (CH); Jerome Charmet, La Chaux-de-Fonds (CH); Thierry Aellen, Neuchatel (CH); Juergen Burger, Neuchatel (CH)

(73) Assignee: Medos International Sarl (CH)

( * ) Notice: Subject to any disclaimer, the term of this patent is extended or adjusted under 35 U.S.C. 154(b) by 83 days.

This patent is subject to a terminal disclaimer.

(21) Appl. No.: 12/854,320

(22) Filed: Aug. 11, 2010

(65) Prior Publication Data

US 2011/0038131 A1    Feb. 17, 2011

Related U.S. Application Data

(60) Provisional application No. 61/233,395, filed on Aug. 12, 2009.

(51) Int. Cl.
B32B 3/00 (2006.01)
B05D 3/00 (2006.01)

(52) U.S. Cl. .......... 428/76; 361/751; 361/752; 361/757; 428/68

(58) Field of Classification Search .......... 428/76, 428/68; 361/751, 752, 757
See application file for complete search history.

(56) References Cited

U.S. PATENT DOCUMENTS

| | | | |
|---|---|---|---|
| 4,206,762 A | 6/1980 | Cosman |
| 4,237,900 A | 12/1980 | Schulman |
| 4,281,667 A | 8/1981 | Cosman |
| 4,676,255 A | 6/1987 | Cosman |
| 4,954,925 A | 9/1990 | Bullis |
| 5,142,912 A | 9/1992 | Frische |
| 5,361,218 A | 11/1994 | Tripp |
| 5,444,901 A | 8/1995 | Wiegand |
| 5,609,629 A | 3/1997 | Fearnot |
| 5,629,008 A | 5/1997 | Lee |
| 6,096,070 A | 8/2000 | Ragheb |
| 6,144,106 A | 11/2000 | Bearinger |
| 6,570,325 B2 | 5/2003 | Graff |
| 6,635,014 B2 | 10/2003 | Starkweather |
| 6,703,462 B2 | 3/2004 | Lee |
| 6,709,715 B1 | 3/2004 | Lang |

(Continued)

FOREIGN PATENT DOCUMENTS

EP 992609 A1 4/2000
WO WO 2006063157 A2 6/2006

(Continued)

OTHER PUBLICATIONS

Balestreri, M. et al; Impact of Intracranial Pressure and Cerebral Perfusion Pressure on Severe Disability and Mortality After Head Injury; Neurocritical Care; 2006; pp. 8-13; vol. 04: Humana Pess Inc.; ISSN 1541-6933/06/4:8-13.

(Continued)

*Primary Examiner* — Brent O'Hern

(57) ABSTRACT

An implantable medical device including a plurality of components on a substrate, and a biocompatible multi-layer coating applied at least in part by vapor deposition to conform to and sealingly cover at least a portion of the components and/or the substrate. The coating is applied in at least two sets of layers, wherein each set has at least one layer formed by dissociation of a polymeric precursor and then deposition of that precursor, and another layer is a biocompatible liquid.

17 Claims, 2 Drawing Sheets

U.S. PATENT DOCUMENTS

| | | | |
|---|---|---|---|
| 6,716,444 | B1 | 4/2004 | Castro |
| 6,774,278 | B1 | 8/2004 | Ragheb |
| 7,007,551 | B2 | 3/2006 | Zdeblick |
| 7,131,334 | B2 | 11/2006 | Mei |
| 7,334,480 | B2 | 2/2008 | Silverbrook |
| 7,347,826 | B1 | 3/2008 | Karicherla |
| 7,364,925 | B2 | 4/2008 | Lee |
| 7,413,547 | B1 | 8/2008 | Lichtscheidl |
| 7,464,598 | B2 | 12/2008 | Silverbrook |
| 7,580,754 | B2 | 8/2009 | Zhang |
| 7,611,533 | B2 | 11/2009 | Bates |
| 2002/0038134 | A1 | 3/2002 | Greenberg |
| 2002/0045921 | A1 | 4/2002 | Wolinsky |
| 2002/0172811 | A1 | 11/2002 | Barth |
| 2002/0185712 | A1 | 12/2002 | Stark |
| 2003/0036794 | A1* | 2/2003 | Ragheb et al. ............... 623/1.15 |
| 2004/0229051 | A1 | 11/2004 | Schaepkens |
| 2006/0083772 | A1 | 4/2006 | DeWitt |
| 2006/0111791 | A1 | 5/2006 | Forsell |
| 2006/0147492 | A1 | 7/2006 | Hunter |
| 2006/0173497 | A1 | 8/2006 | Mech |
| 2007/0096281 | A1 | 5/2007 | Greenberg |
| 2007/0128420 | A1 | 6/2007 | Maghribi |
| 2007/0158100 | A1 | 7/2007 | Greenberg |
| 2007/0216300 | A1 | 9/2007 | Lee |
| 2008/0051862 | A1 | 2/2008 | Mech |
| 2008/0132992 | A1 | 6/2008 | Bates |
| 2008/0185173 | A1 | 8/2008 | Bedinger |
| 2008/0200750 | A1 | 8/2008 | James |
| 2008/0306554 | A1 | 12/2008 | McKinley |
| 2009/0004241 | A1 | 1/2009 | Ho |
| 2009/0036754 | A1 | 2/2009 | Pons |
| 2009/0110892 | A1 | 4/2009 | Erlat |
| 2009/0124965 | A1 | 5/2009 | Greenberg |
| 2009/0142227 | A1 | 6/2009 | Fuchs |
| 2009/0192580 | A1 | 7/2009 | Desai |
| 2009/0254146 | A1 | 10/2009 | Bonmassar |
| 2009/0263581 | A1 | 10/2009 | Martin, III |
| 2009/0263641 | A1 | 10/2009 | Martin, III |
| 2009/0288876 | A1 | 11/2009 | Bedinger |
| 2009/0291200 | A1 | 11/2009 | Bedinger |
| 2009/0297813 | A1 | 12/2009 | Erlat |
| 2010/0005851 | A1 | 1/2010 | Cottles |
| 2011/0015686 | A1 | 1/2011 | Kara |
| 2011/0038130 | A1 | 2/2011 | Hogg |
| 2011/0038131 | A1 | 2/2011 | Hogg |
| 2011/0039050 | A1 | 2/2011 | Hogg |

FOREIGN PATENT DOCUMENTS

| | | | |
|---|---|---|---|
| WO | WO 2008039543 | A1 | 4/2008 |

OTHER PUBLICATIONS

Bork, T. et al; Development and in-vitro characterization of an implantable flow sensing transducer for hydrocephalus; Biomedical Microdevices, vol. 12, No. 4, 607-618, DOI: 10.1007/s10544-010-9413-6; SpringerLink Date: Mar. 13, 2010.

Boyd, B.; Advanced coating technologies for lead-free solders; Global SMT & Packaging. Jun. 2007, pp. 10-12; www.globalsmt.net.

Callahan, Russell R.A. et al; Downstream oxygen etching characteristics of polymers from the parylene family; J. Vac. Sci. Technol. B, pp. 1496-1500; vol. 21, No. 4, Jul./Aug. 2003; © 2003 American Vacuum Society.

Chang, T.Y. et al; Cell and Protein Compatibility of Parylene-C Surfaces; Langmuir, 2007; pp. 11718-11725; vol. 23, No. 23; 2007 American Chemical Society Published on Web Oct. 4, 2007.

Chiang, C.C. et al; Deposition and permeation properties of SiNX/ parylene multilayers on polymeric substrates; Surface & Coatings Technology 200 (2006) pp. 5843-5848; www.sciencedirect.com.

Czosnyka, M., et al; Monitoring and interpretation of intracranial pressure; J. Neurol. Neurosurg. Psychiatry 2004;75; pp. 813-821; Downloaded from jnnp.bmj.com on Sep. 2, 2009; DOI:10.1136/jnnp.2003.033126.

Czosnyka, M., et al; Monitoring of Cerebrovascular Autoregulation: Facts, Myths, and Missing Links; Neurocrit Care (2009) 10 pp. 373-386; Humana Press DOI 10.1007/s12028-008-9175-7.

Hsu, Jui-Mei et al.; Characterization of Parylene-C film as an encapsulation material for neural interface devices; 4M Network of Excellence, 4M Knowledge base—papers; Submitted on Nov. 12, 2007—16:23. http://www.4m-net.org/files/papers/4M2007/374451/PID374451.pdf.

Kokko, K., et al; Composite coating structure in an implantable electronic device; Soldering & Surface Mount Technology; vol. 21 No. 3 (2009); pp. 24-29 © Emerald Group Publishing Limited [ISSN 0954-0911].

Kumar, R: Advances in Adhesion Solutions for Medical Applications; Proceedings of the SMTA Medical Electronics Symposium, Jan. 29-31, 2008, Anaheim, California, USA; rkumar@scscoatings.com.

Pruden, K.G. et al; Characterization of Parylene-N and Parylene-C Photooxidation; Journal of Polymer Science: Part A: Polymer Chemistry, pp. 1486-1496; vol. 41, (2003) © 2003 Wiley Periodicals, Inc.

Pruden, K.G. et al; Ammonium chloride complex formation during downstream microwave ammonia plasma treatment of parylene-C; J. Vac. Sci. Technol. A, Nov./Dec. 2005; pp. 1605-1609; vol. 23, No. 6,.

Sadhir, R.K.et al.; The adhesion of glow-discharge polymers, Silastic and Parylene to implantable platinum electrodes: results of tensile pull tests after exposure to isotonic sodium chloride; Biomaterials 1981, pp. 239-243, vol. 2, October.

Seong, J.W. et al; Effects of ion bombardment with reactive gas environment on adhesion of Au films to Parylene C film; Thin Solid Films 476 (2005) pp. 386-390; © 2004 Elsevier B.V.; www.sciencedirect.com.

Stieglitz, T., et al; Encapsulation of Flexible Biomedical Microimplants with Parylene C; Fraunhofer-Institute for Biomedical Engineering; thomas.stieglitz@ibmt.fhg.de; https://ifess.org/ifess02/stimulation_technology/StieglitzT1.pdf.

Tewari, P. et al; Control of interfaces on electrical properties of Si02—Parylene-C laminar composite dielectrics; Journal of Colloid and Interface Science 332 (2009) pp. 65-73.

Von Elm, Erik, et al; Severe traumatic brain injury in Switzerland—feasibility and first results of a cohort study; Swiss Med Wkly 2008;138 (23-24): pp. 327-334 • www.smw.ch.

Zhang, X., et al; Crystallinity properties of parylene-n affecting its use as an ILD in submicron integrated circuit technology; Thin Solid Films 270 (1995) pp. 508-511; Elsevier Science S.A.

Ruckh, R. et al; Model Calculation of Polymer Heterostructures; Physica Scripta. 1988; pp. 122-124; vol. 38, Institute of Physics Publishing (IOP) on behalf of the Royal Swedish Academy of Sciences; Academies of Sciences and Physical Societies; Sweden.

Sworecki, K. et al; Modification of Polymer Membranes by Ion Implantation; Nuclear Instruments and Methods in Physics Research; (2004); B 225; pp. 483-488; 2004 Elsevier B.V.

Kumar, R.; New Developments in Parylene Technology for Medical Electronics Advancement; Proceedings of the SMTA Medical Electronics Symposium; May 15-17, 2006; pp. -9; Bloomington. Minnesota. USA.

Affinito, J.D. et al; A New Method for Fabricating Transparent Barrier Layers; Thin Solid Films (1996); pp. 63-67; 290-291; 1996 Published by Elsevier Science S.A.

Nicholas, M.F. et al; Functional Hermetic Encapsulation of Integrated Circuits; ISA, 1991—pp. 331-339; Paper 091-043 0067-8856/91; ISA Publishing; Research Triangle Park, NC, USA; The British Library, UK.

North, B.; Intracranial Pressure Monitoring; Head Injury; 1997; pp. 209-216; 10; Chapman & Hall, London.

Khabari, A. et al: Partially Ionized Beam Deposition of Parylene; Journal of Non-Crystalline Solids (2005); pp. 3536-3541; vol. 351; 2005 Elsevier B.V.

Li, P.-Y, et al; A Parylene Bellows Electrochemical Actuator for Intraocular Drug Delivery; Transducers Jun. 21-25, 2009; pp. 1461-1464; 978-1-4244-4193-8/09; IEEE 2009, Piscataway, NJ, USA.

Pang, C.; Parylene Technology for Neural Probes Applications; Thesis for the Degree of Doctor of Philosophy; Sep. 17, 2007; pp. vii-viii and pp. 1-139; California Institute of Technology, Pasadena, CA, USA 2008.

Wolgemuth, L.; Parylenes: Advanced Polymers for Medical Devices; Specialty Coating Systems, 2006; pp. 1-4; 7645 Woodland Drive, Indianapolis, IN 46278 USA; lwolgemuth@scscoatings.com.

Zakar, E. et al; Patterning of Thick Parylene Films by Oxygen Plasma for Application as Exploding Foil Initiator Flyer Material; Army Research Laboratory; Sep. 2009; pp. 1-13; ARL-TR-4956; Adelphia, MD 20783-1197.

Callahan, R. et al.; Etching parylene-N using a remote oxygen microwave plasma; J. Vac. Sci. Technol. B, Sep./Oct. 2002; pps. vol. 20, No. 5; pp. 1870-1877; © 2002 American Vacuum Society.

Codman® ICP Monitoring System Quick set-up Guide; Product Brochure © 2001 Codman & Shurtleff, Inc.

Feili, D. et al.; Flexible organic field effect transistors for biomedical microimplants using polyimide and parylene C as substrate and insulator layers; J. Micromech. Microeng. (2006); pp. 1555-1561; 16; Institute of Physics Publishing.

Hambrecht, F.T.; Biomaterials research in neural prostheses; Biomaterials Jul. 1982; pp. 187-188, vol. 3; Butterworth & Co (Publishers) Ltd.

Hemedex® Cerebral Blood Flow Monitoring System; Product Brochure © 2007 Codman & Shurtleff, Inc.

Huang, Sheng-Jean, et al.; Clinical outcome of severe head injury using three different ICP and CPP protocol-driven therapies; Journal of Clinical Neuroscience (2006)pp. 818-822; 13; Elsevier Ltd.

ICP Express™; Product Brochure © 2001 Codman & Shurtleff, Inc.

Khabari, A., Partially ionized beam deposition of parylene; Journal of Non-Crystalline Solids (2005); pp. 3536-3541; 351; Elsevier B.V.

Lahann, J.; Vapor-based polymer coatings for potential biomedical applications; Polymer International (2006); pp. 1361-1370; 55; 2006 Society of Chemical Industry.

Lee, L. James; Polymer Nanoengineering for Biomedical Applications; Annals of Biomedical Engineering, Jan. 2006; pp. 75-88; vol. 34, No. 1.

Mark, Herman F.; Xylylene Polymers; Concise Encyclopedia of Polymer Science and Technology; 2007; pp. 1384-1389, John Wiley & Sons, USA 2007.

Mitu, B., et al; Plasma-deposited parylene-like thin films: process and material properties; Surface and Coatings Technology (2003), pp. 174-175; Issue 124-130; Elsevier Science B.V; www.sciencedirect.com.

Rodger, D.C.; et al.; Flexible parylene-based multielectrode array technology for high-density neural stimulation and recording; Sensors and Actuators B (2008); pp. 449-460; 132; Elsevier B.V.

Senkevich, J.J. et al.; The facile surface modification of poly(p-xylylene) ultrathin Films; Colloids and Surfaces A: Physicochem. Eng. Aspects; (2003); pp. 167-173; 216; Elsevier Science B.V.

Seymour, John P, et al; The insulation performance of reactive parylene films in implantable electronic devices; Biomaterials (2009); pp. 6158-6167; 30; Elsevier Ltd.

Wolgemuth, L.; A Look at Parylene Coatings in Drug-Eluting Technologies; Reprinted from Medical Device & Diagnostic Industry, Aug. 2005; Copyright © 2005 Canon Communications LLC.

Yamagishi, F. G.; Investigation of Plasma-Polymerized Films as Primers for Parylene-C Coatngs on Neural Prosthesis Materials; Metallurgical and Protective Layers Thin Solid Films, (1991) pp. 39 50; 202; Elsevier Sequoia/Printed in The Netherlands.

Yu, Qingsong et al.; Engineering the surface and interface of Parylene C coatings by low-temperature plasmas; Progress in Organic Coatings; (2001); pp. 247-253; 41; 2001 Elsevier Science B.V.

Affinito, John., et al; Vacuum deposited polymer / metal multilayer films for optical application; Thin Solid Films; (1995); pp. 43-48; vol. 270; © 1995 Elsevier Science S.A., US.

Blenkiewicz, J.; Plasma-Enhanced Parylene Coating for Medical Device Applications; Medical Device Technology; Jan./Feb. 2006; pp. 10-11; vol. 17. No. 1; www.medicaldevicesonline.com; US.

Charlson, E.M. et al; Temperature Selective Deposition of Parylene-C; IEEE Transactions on Biomedical Engineering; Feb. 1992; pp. 202-206; vol. 39, No. 2; IEEE, Piscataway, NJ US.

Chou, Chia-Man, et al; Preparation of Plasma-Polymerized Para-Xylene as an Alternative to Parylene Coating for Biomedical Surface Modification; Surface & Coatings Technology (2010); pp. 1631-1636; vol. 204; Elsevier Science B.V; www.elsevier.com/locate/surfcoat, US.

Dribinskiy, Stanislav F. et al; Properties of Various Polyparylenes Deposited by Chemical Vapor Deposition; Paper PS3-TuP12; AVS 53rd International Symposium; Nov. 14, 2006; pp. 1-4; University of Applied Sciences, D-80335 Munich and Plasma-Parylene Coating Services, D-83022 Rosenheim; DE.

Heetderks, Wiluam J.; RF Powering of Millimeter- and Submillimeter-Sized Neural Prosthetic Implants; IEEE Transactions on Biomedical Engineering; May 1988; pp. 323-327; vol. 35, No. 5; IEEE, Piscataway, NJ US.

Meng, E. et al; Plasma Removal of Parylene C; J. Micromech. Microeng. (2008), pp. 1-13; 18 045004; IOP Publishing; http://iopscience.iop.org, US.

Mitu, B., et al; Plasma-Deposited Parylene-Like Thin Films: Process and Material Properties; Surface and Coatings Technology; (2003) pp. 124-130; 174-175; Elsevier Science B.V; www.sciencedirect.com, US.

Momentive Performance Materials: Silquest A-174* Silane Product Brochure; Copyright 2003-2007 Momentive Performance Materials Inc., Wilton, CT, USA.

Ratanalert, Sanguansin, M.D. et al; ICP Threshold in CPP Management of Severe Head Injury Patients; Surg. Neurol.; 2004; pp. 429-434; 61; © 2004 Elsevier Inc. 360 Park Avenue South, New York, NY 10010-17.

Ratier, Bernard; Vapor Deposition Polymerization and Reactive Ion Beam Etching of poly(p-xylylene) Films for Waveguide Applications; Optical Materials; (1999); pp. 229-233; vol. 12; 1999 Elsevier Science B.V.

Seymour, John P., et al; Neural Probe Design for Reduced Tissue Encapsulation in CNS; Biomaterials; (2007); pp. 3594-3607; vol. 28, Issue 25; doi:10.1016/i.biomaterials.2007.03.024; Copyright © 2007 Elsevier Ltd, US.

V&P Scientific, Inc; Solvent Resistance of Parylenes C,N,D; Technology Letter #10; Revised May 1985; Copyright © 2009, V&P Scientific, Inc. San Diego, CA; http://www.vp-scientific.com/solvent.htm.

Wolgemuth, Lonny; A Look at Parylene Coatings in Drug-Eluting Technologies; Medical Device & Diagnostic Industry; Aug. 1, 2005; Copyright © 2005 Medical Device & Diagnostic Industry.

Wolgemuth, Lonny; The Truly Conformal Coating; Medical Device Developments; Apr. 4, 2008; 2 pages; vol. 1; http://www.medicaldevice-network.com/features/feature1818/; Copyright 2011 Net Resources International US.

Wright, Dylan, et al; Reusable, Reversibly Sealable Parylene Membranes for Cell and Protein Patterning; Journal of Biomedical Materials Research Part A; May 2008; pp. 530-538; vol. 85A; Article first published online: Aug. 29, 2007; Copyright © 2007 Wiley Periodicals, Inc., A Wiley Company; http://onlinelibrary.wiley.com/doi/10.1002/jbm.a.31281/abstract.

Xingding, Zhang; The relationship between GCS, ICP, CPP and glutamate in the cerebrospinal fluid following acute cerebral injury and brain edema in humans; Head Injury—Pathophysiology of Head Injury; Jul. 7, 1997; p. S71; P-2-159;.

* cited by examiner

PACKAGING WITH ACTIVE PROTECTION LAYER

CROSS-REFERENCE TO RELATED APPLICATION

This application claims priority to U.S. Provisional Application No. 61/233,395 by Burger et al. filed Aug. 12, 2009 entitled "Ultrathin Multilayers for a Hermetic Packaging". The following applications, filed concurrently herewith, are incorporated herein by reference: U.S. patent application Ser. No. 12/854,298 entitled "Ultra-Thin Multi-Layer Packaging" by Hogg et al.; and U.S. patent application Ser. No. 12/854,304 entitled "Plasma Enhanced Polymer Ultra-Thin Multi-Layer Packaging" by Hogg et al.

BACKGROUND OF THE INVENTION

1. Field of the Invention

The invention relates to hermetic biocompatible packaging and more particularly to packaging that is deposited in successive layers, including at least one biocompatible liquid layer, over three-dimensional structures.

2. Description of the Related Art

Packaging which is cost-effective and compatible with miniaturization is an important factor in the production of an implantable medical device. There is a need for a reliable, cost-effective batch-manufacturing packaging process such as a wafer level packaging, to protect components such as electronic- and mechanical components, micro-electronic- and mechanical systems, micro-electro-mechanical systems and substrates carrying such components. The mentioned packaging must be mechanically and chemically stable to protect the body tissue from potentially toxic dissolvents, and also to protect the components of the implanted device from corrosion or degradation created by bodily fluids.

Encapsulation of organic light emitting diodes by at least one barrier stack is disclosed in U.S. Pat. No. 6,570,325 by Graff et al. The barrier stack includes at least one barrier layer and at least one decoupling layer. Other protective barriers which include parylene for opto-electronic devices are disclosed by Lee et al. in U.S. Patent Application Publication Nos. 2005/0146267, now U.S. Pat. No. 7,364,925, and 2007/0216300, now abandoned.

Techniques for protecting integrated circuits using copolymers formed of parylene N and co-monomers with various double bonds is disclosed by Lang et al. in U.S. Pat. No. 6,709,715. Other, more recent coating techniques utilizing parylene are disclosed by Bedinger et al. in U.S. Patent Application Publication No. 2009/0291200 and by Martin, III et al. in U.S. Patent Application Publication Nos. 2009/0263581 and 2009/0263641.

A plastic membrane device having micro-structures such as micro-lenses, micro-channels and waveguides utilizing a liquid are disclosed in U.S. Patent Application Publication No. 2009/0246546 by Keppner et al.

It is therefore desirable to provide improved hermetic biocompatible packaging, especially for implantable medical devices for which reduction in size is preferred.

SUMMARY OF THE INVENTION

An object of the present invention is to provide improved, lower-cost multi-layer packaging having low permeability to bodily fluids to protect both the patient and components beneath the packaging.

Another object of the present invention is enable the implementation of at least one active agent set in the biocompatible hermetic coating.

A still further object of the present invention is to provide such packaging which can be applied to medical devices substantially at room temperature to protect the medical devices against temperature defects which may otherwise occur at higher application temperatures.

This invention features an implantable medical device including a plurality of components on a substrate, and a biocompatible multi-layer coating applied at least in part by vapour deposition to conform to and sealingly cover at least a portion of the components. The coating is applied in at least two sets of layers, wherein each set has at least one layer formed by dissociation of a polymeric precursor and then deposition of that dissociated precursor, and another layer is a biocompatible liquid.

In a number of embodiments, each layer differs in at least one diffusion barrier property from the other layer in the set. In some embodiments, diffusion through each layer differs from that of the other layer in the set and adds to the overall barrier effect of the coating. In one embodiment, the polymeric layer itself is activated for enhanced wetability. In certain embodiments, the precursor for at least one layer is selected from di-p-xylylene and halogenated derivatives thereof to form a type of parylene for that layer. In one embodiment, at least one of the layers in each set is a plasma-enhanced parylene polymer.

In some embodiments, each of the sets has at least three layers, and diffusion through each layer differs from that of the other layers in the set. In one embodiment, at least one of the layers enhances wetability of the layer beneath it, and the wetability-enhancing layer includes at least one of chemical and plasma activation of the layer beneath it.

In another embodiment, the liquid is applied by condensation. In yet another embodiment, the liquid is applied as a fog or a mist. In a still further embodiment, the liquid is applied by dipping or casting. The liquid itself acts as an active protection layer by providing a physical and/or chemical barrier to oxygen, water and/or types of ions, atoms or molecules in a bi-directional manner; in some embodiments, at least one liquid layer also includes an active agent such as a pharmaceutical, antimicrobial or other material having a physiological property or activity. In one embodiment, the multi-layer coating conforms to and sealingly covers at least substantially all of the components, some or all of which may be three-dimensional, and may cover some or all of the substrate as well.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

Figure 1:
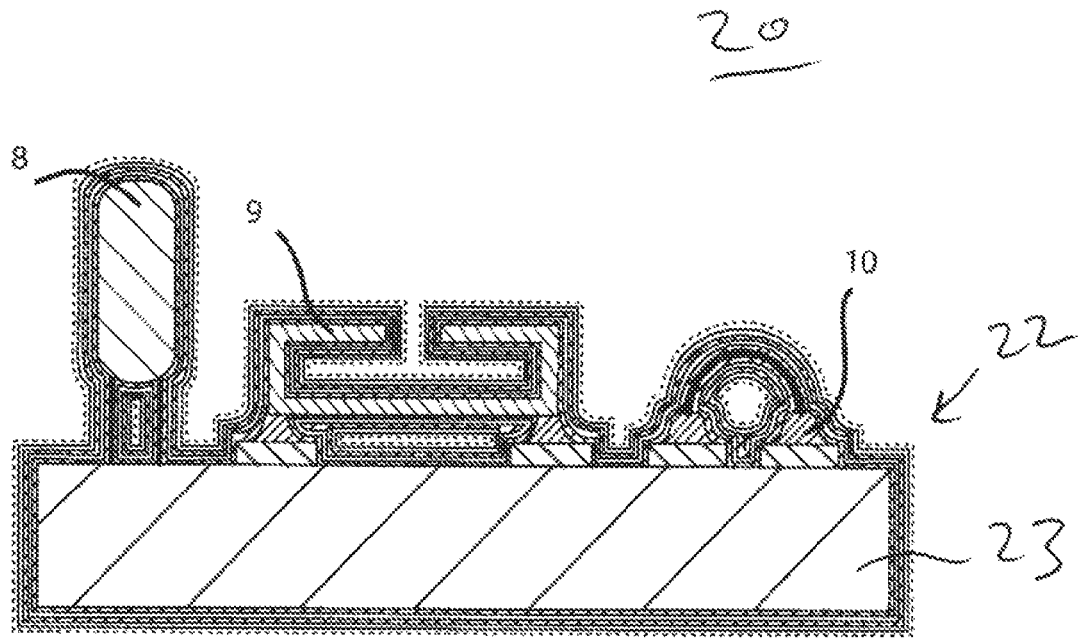
FIG. 1 is a schematic cross-sectional view of complex, three-dimensional components and a substrate coated with multiple layers according to the present invention.

FIG. 1 illustrates an example of components and a substrate of an implantable medical device 20 with three-dimensional conformal packaging according to the present invention. Device 20 includes a plurality of three-dimensional components, such as transistor 8, micro-electro-mechanical system 9 and conductive bonding 10, on a substrate 23 which can be flexible or rigid as desired. A biocompatible multilayer coating 22 applied at least in part by vapour deposition conforms to and sealingly covers at least a portion of the components 8,9,10 and the substrate 23.

Figure 2:
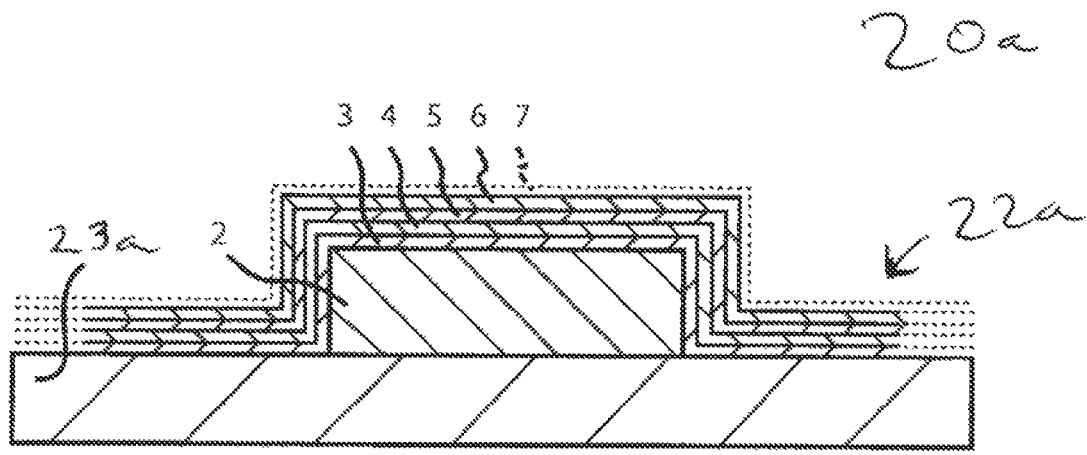
FIG. 2 is an enlarged cross-sectional view of multiple layers according to the present invention protecting a component on a substrate.

The coating 22 is applied in at least two sets of layers, wherein each set has at least one layer formed by dissociation of a precursor and then deposition of that dissociated precursor, also referred to as deposition of dissociated species of the precursor, and the other layer is a biocompatible liquid. In some constructions, at least one of the layers is formed by at least one of plasma dissociation and excitation of the precursor to form a plasma-enhanced precursor, and then deposition of the plasma-enhanced precursor. As illustrated schematically in FIG. 2, coating 22a is formed in a series of layers 3, 4, 5, and 6 over component 2 of device 20a with substrate 23a. Additional layers 7 et cetera can be added as desired. At least two sets of layers, such as layers 3 plus 4 and 5 plus 6, have one layer each, such as layers 4 and 6, that are formed of a liquid as described below. In other constructions, each set has at least three layers, such as layers 3, 4 and 5 in a first set and layers 6, 7 and 7' (not shown) in a second set, with one of layers 4 and 5 being a liquid and one of layers 7 and 7' being a liquid. Typically, the outermost layer is a solid layer to retain liquids beneath it or to allow a well-defined diffusion of the liquid beneath it. In some constructions, an additional treatment, such as a gas plasma, or an additional layer is added to improve the interface between non-liquid layers, especially with respect to impurity diffusion.

It is a realization of the inventors that increasing the number and type of thinner layers, rather than having fewer, thicker layers, enhances overall barrier properties of packaging according to the present invention due to the increased number of layer interfaces. In other words, the sum of the interfaces dominates diffusion behaviour, and therefore the overall barrier effect of the coating, more than the sum of the thicknesses of the layers. This may also be expressed as the diffusion barrier being composed by the layer interface and each layer itself. As for the physical properties of each layer, polymers such as parylene are especially desirable for being pin-hole-free, homogenous, and stress-free, which is especially advantageous to overlie a liquid layer. The use of one or more liquid layers according to the present invention, and the additional solid/liquid interfaces provided thereby, further adds unique liquid properties to the overall barrier effect of the coating.

Figure 3:
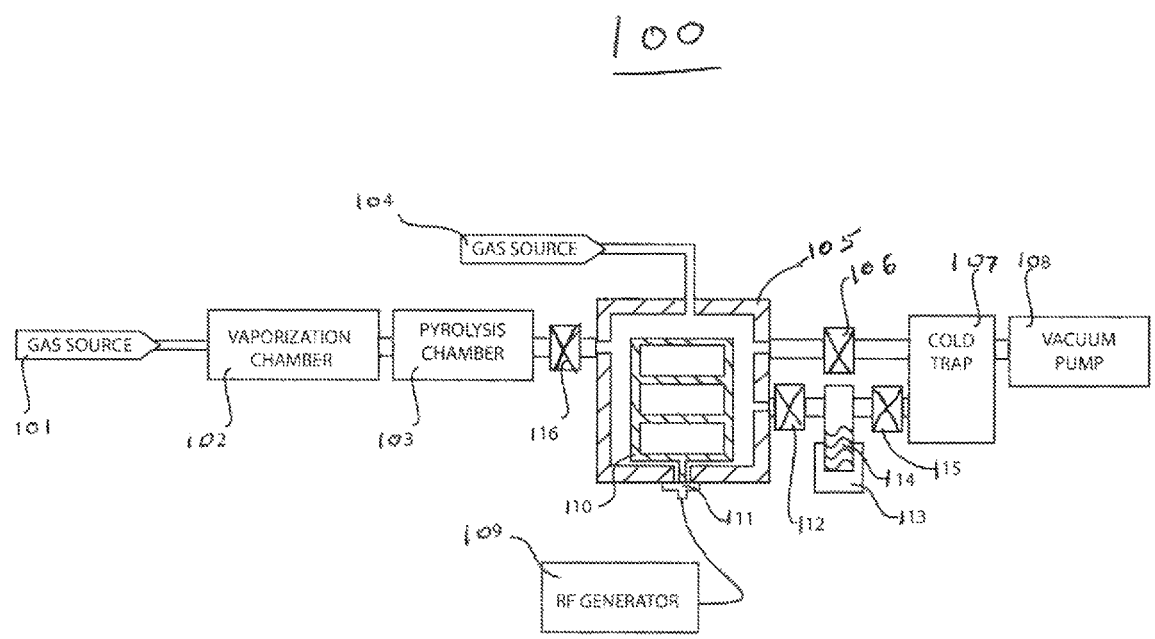
FIG. 3 is a schematic diagram of a reactor system for producing multi-layer packaging according to the present invention.

One system 100 for achieving such conformal packaging with multi-layer coatings is shown in FIG. 3. Deposition reactor chamber 105 can be utilized for a thermal process, such as a conventional or modified Gorham process, or a plasma enhanced process. For the deposition of a parylene on a liquid layer with a vapour pressure lower than 7 Pa, the conventional Gorham process is used. Modified Gorham process (such as atmospheric pressure chemical vapour deposition) is used for the deposition of parylene on a liquid layer with a liquid vapour pressure greater than 7 Pa. In that situation, an inert carrier gas from gas source 101 is utilized to transport the polymeric dimer and monomer through vaporization chamber 102 and pyrolysis chamber 103 to the reactor chamber 105. The injection of an inert gas increases the pressure in the reactor chamber. This protects the liquid layer against vaporization. Suitable inert gases are argon, helium, and nitrogen, for example.

For the conventional thermal deposition process, such as for parylene deposition, the vaporization chamber 101 vaporizes a solid parylene precursor, for example a stable di-cyclic dimer, di-p-xylylene, or halogenated derivatives at temperatures between 110° and 200° C. The vaporized precursor then passes to the pyrolysis chamber 102 to decompose the dimer in reactive species, such as monomers, at temperatures between 400° C. and 700° C. For dichloro-p-xylylene, typical parameters are 150° C. for the vaporization and 650° C. for the pyrolysis. The pyrolyzed precursor then passes from the pyrolysis chamber 103 to the medical devices to be treated on a sample holder 110 in the deposition chamber 105. Typical parylene layer thickness is between 10 nm-100 microns. The precursor vapour pressure in the deposition chamber 105 is approximately between 1 and 10 Pa, typically 7 Pa, and the substrate temperature is substantially at room temperature. The remaining vapour mixture then passes from deposition chamber 105 through valve 106 to a cold trap 107 connected to a vacuum pump 108. For polymer deposition the valves 116 and 106 are open.

For liquid layer deposition, valves 116 and 106 are closed. In a number of constructions, the liquid to be deposited on the medical devices is placed in liquid chamber 114. Evaporation of the liquid is controlled through energy source 113 such as a thermal system or an ultraviolet light source system. The evaporation rate can be controlled through the amount of energy introduced from energy source 113 to the liquid chamber 114. Another factor for the quantity of the vaporized liquid to be introduced depends on the size of the liquid chamber 114. Typically, a thin homogeneous pinhole-free liquid layer of 10 nm to 500 microns is desirable. During liquid layer deposition, valve 112 is open. The energy source 113 evaporates the liquid, which then condenses on the medical devices placed on sample holder 110. The valve 115 allows pumping the liquid chamber 114 regardless of the deposition chamber 105. To protect the vacuum pump 108, fluid exiting through valve 115 passes through cold trap 107.

In some constructions, co-evaporation of specific species is obtained, such as by combining elements chemically or physically with a type of parylene or other polymer simultaneously. In that situation, valves 116 and 106 remain open while valve 112 is open.

In other constructions, the liquid is applied as a fog or a mist. In still further constructions, the liquid is applied by dipping, casting or dispensing. In this situation, the medical devices having a least one protective layer already deposited on them are taken out of reactor 105 and dipped or otherwise treated with liquid. The medical devices are then raised above or away from the liquid to drain excrescent liquid, for an amount of time that depends on the desired thickness of the liquid layer. When additional protective layers are to be deposited, then the medical devices are returned to the reactor 105. The process can be reiterated until the desired behavior and thickness of hermetic barrier is achieved.

The liquid or liquids selected for use according to the present invention should be biocompatible to protect patients from inflammation or other hazardous tissue reaction in the event of defects arising in one or more layers. The liquid, such as a biocompatible oil, should have good wetability properties to create a thin, conformal homogeneous pinhole-free liquid layer of typically 10 nm to 500 microns on an underlying polymeric or inorganic layer. Depending on the hydrophobic-hydrophilic, lipophobic-lipophilic and/or other properties of the liquid, the medical device coated according to the present invention is more readily protected against corrosion and/or degradation, etc. The liquid or liquids can also provide a storage function, such as by absorbing specific atoms, ions or molecules like oxygen, water and/or types of molecules. Such properties are bi-directional, thereby protecting the patient as well as whatever components and substrate of the medical device are coated according to the present invention. For certain medical applications, at least one liquid layer contains at least one pharmaceutical or other active agent to protect against infection and/or inflammation, or to improve implant-tissue adhesion or acceptance. An outer layer such as an amorphous structure, such as an amorphous parylene layer, can serve as a drug releasing membrane to provide controlled release of an active agent through the amorphous layer. The amorphous layer can by created for example by a plasma enhanced chemical vapour deposition.

An in-situ plasma enhanced chemical vapour deposition process can also be utilized. Controlled plasma is formed adjacent to the medical device wafers by RF energy applied to sample holder 110 from RF generator 109, with the deposition chamber 105 grounded, via a high frequency sealed by a pass-through connector 111. RF generator 109 can supply at a high RF frequency of typically 13.56 MHz or 2.45 GHz to the sample holder 110 to enhance the decomposition and/or excitation of reactive species introduced into chamber. A gas source 104 is connected to deposition chamber 105 to introduce one or more gases in the plasma process, for surface treatment or precursor interaction, such as recombination, excitation or dissociation.

Layer on substrate adhesion or layer on layer adhesion could be improved by different processes. Typically for parylene adhesion, either on substrate or on layer, but not limited to, silanization or gas plasma treatment are used. For example oxygen, nitrogen or air plasma is applied directly in the deposition chamber 103 before coating. Further, other adhesion layer or plasma enhanced deposition layer can be used. Preferably, a well known adhesion layer based on silanes are composed of vinyl trichlorosilane in either xylene, isopropyl alcohol or a chlorofluorocarbon gas. Alternatively, gammamethacryloxypropyltrimethoxysilane in a methanol-water solvent have been successfully used. Silanes can also be vapour phase applied if non-liquid application is preferred.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable medical device comprising:
    a plurality of components on a substrate; and
    a biocompatible multi-layer coating applied at least in part by vapour deposition to conform to and sealingly cover at least a portion of the components and the substrate, the coating being applied in at least two sets of layers, wherein each set has at least one layer formed by dissociation of a polymeric precursor and then deposition of that dissociated precursor, and another layer is a biocompatible liquid, and further wherein each of the sets has at least three layers, and diffusion through each layer differs from that of the other layers in the set.

2. The implantable medical device of claim 1 wherein each layer differs in at least one diffusion barrier property from the other layer in the set.

3. The implantable medical device of claim 1 wherein diffusion through each layer differs from that of the other layer in the set and adds to the overall barrier effect of the coating.

4. The implantable medical device of claim 1 wherein the precursor for at least one set is selected from di-p-xylylene and halogenated derivatives thereof.

5. The implantable medical device of claim 4 wherein the precursor is dichloro-p-xylylene.

6. The implantable medical device of claim 1 wherein at least one of the layers enhances wetability of the layer beneath it.

7. The implantable medical device of claim 6 wherein the wetability-enhancing layer includes at least one of chemical and plasma activation of the layer beneath it.

8. The implantable medical device of claim 1 wherein the liquid is applied by condensation.

9. The implantable medical device of claim 1 wherein the liquid is applied as a fog or a mist.

10. The implantable medical device of claim 1 wherein the liquid is applied by dipping or casting.

11. The implantable medical device of claim 1 wherein at least one of the layers in each set is a plasma-enhanced parylene polymer.

12. The implantable medical device of claim 1 wherein at least one liquid layer includes an active agent.

13. The implantable medical device of claim 1 wherein the plurality of components have at least a first three-dimensional portion, and the coating conforms to and sealingly covers at least the first portion of the components.

14. The implantable medical device of claim 13 wherein the multi-layer coating conforms to and sealingly covers at least substantially all of the components.

15. The implantable medical device of claim 1 wherein a barrier property for the transport of impurities is dominated more by the interface between adjacent layers than by the thickness of each individual layer.

16. An implantable medical device comprising:
    a plurality of components on a substrate having at least a first three-dimensional portion; and
    a biocompatible multi-layer coating applied at least in part by vapour deposition to conform to and sealingly cover at least the first portion of the components and the substrate, the coating being applied in at least two sets of layers, wherein each set has at least one layer formed by dissociation of a polymeric precursor and then deposition of that dissociated precursor, and another layer is a biocompatible liquid, and wherein a barrier property for the transport of impurities is dominated more by the interface between adjacent layers than by the thickness of each individual layer, and further wherein each of the sets has at least three layers, and diffusion through each layer differs from that of the other layers in the set.

17. The implantable medical device of claim 16 wherein the multi-layer coating conforms to and sealingly covers at least substantially all of the components and the substrate.

* * * * *